United States Patent
Windolf

(10) Patent No.: US 9,451,983 B2
(45) Date of Patent: Sep. 27, 2016

(54) CANNULA AND KIT FOR EVALUATION AND PREPARATION OF BONE TISSUE

(75) Inventor: Markus Windolf, Davos (CH)

(73) Assignee: AO TECHNOLOGY AG, Chur (CH)

( * ) Notice: Subject to any disclaimer, the term of this patent is extended or adjusted under 35 U.S.C. 154(b) by 344 days.

(21) Appl. No.: 14/110,254

(22) PCT Filed: Apr. 19, 2011

(86) PCT No.: PCT/CH2011/000086
§ 371 (c)(1),
(2), (4) Date: Oct. 7, 2013

(87) PCT Pub. No.: WO2012/142716
PCT Pub. Date: Oct. 26, 2012

(65) Prior Publication Data
US 2014/0031794 A1   Jan. 30, 2014

(51) Int. Cl.
A61B 17/34      (2006.01)
A61B 17/88      (2006.01)
A61B 17/16      (2006.01)
A61B 17/3205    (2006.01)

(52) U.S. Cl.
CPC ........... *A61B 17/3472* (2013.01); *A61B 17/34* (2013.01); *A61B 17/3417* (2013.01); *A61B 17/3468* (2013.01); *A61B 17/8805* (2013.01); *A61B 17/8811* (2013.01); *A61B 17/1615* (2013.01); *A61B 17/32053* (2013.01);
(Continued)

(58) Field of Classification Search
CPC ........... A61B 17/32053; A61B 17/34; A61B 17/3417; A61B 17/3468; A61B 2017/347; A61B 17/3472; A61B 2017/348; A61B 2017/3482; A61B 2017/3488; A61B 2017/349; A61B 17/8805; A61B 17/8811; A61B 17/8816; A61B 17/8819
See application file for complete search history.

(56) References Cited

U.S. PATENT DOCUMENTS 2,919,692 A  *  1/1960  Ackermann  .........  A61B 10/025
                                                600/567
5,921,987 A  *  7/1999  Stone  .................  A61B 17/1637
                                                606/79
(Continued)

FOREIGN PATENT DOCUMENTS

FR    2885512 A1   11/2006
WO    2006062916 A2   6/2006
WO    2009125243 A1  10/2009

OTHER PUBLICATIONS

International Preliminary Report on Patentability dated Oct. 31, 2013 in corresponding International Patent Application No. PCT/CH2011/000086, filed Apr. 19, 2011.

*Primary Examiner* — Larry E Waggle, Jr.
(74) *Attorney, Agent, or Firm* — Rankin, Hill & Clark LLP

(57) ABSTRACT

A cannula with a proximal end, a distal end and a lumen penetrating from the proximal end to the distal end. The cannula includes a shaft portion including a rear end and a front end, a tip portion coaxially extending from the front end of the shaft portion to the distal end of the cannula, and a cutting edge. A coupling portion, which is suitable for being connected to a surgical tool or instrument, is terminally arranged towards the proximal end of the cannula and extends to the rear end of the shaft portion. A removable obturator is insertable in the lumen. The obturator seals the lumen at the distal end of the cannula. A method for improved fracture fixation using the cannula, a method for intraoperative surgical decision making using the cannula and a method for irrigation of bone tissue and subsequent injection of bone cement using the cannula.

42 Claims, 5 Drawing Sheets

(52) U.S. Cl.
CPC ........ *A61B17/8816* (2013.01); *A61B 17/8819* (2013.01); *A61B 17/8897* (2013.01); *A61B 2017/347* (2013.01); *A61B 2017/348* (2013.01); *A61B 2017/349* (2013.01); *A61B 2017/3482* (2013.01); *A61B 2017/3488* (2013.01); *A61B 2090/066* (2016.02)

(56) References Cited

U.S. PATENT DOCUMENTS

| | | | |
|---|---|---|---|
| 6,241,734 B1* | 6/2001 | Scribner | A61B 17/8816 606/93 |
| 6,575,919 B1* | 6/2003 | Reiley | A61B 17/34 600/567 |
| 6,582,446 B1 | 6/2003 | Marchosky | |
| 6,749,595 B1* | 6/2004 | Murphy | A61B 17/8811 604/500 |
| 7,081,123 B2* | 7/2006 | Merboth | A61B 10/025 600/565 |
| 7,935,122 B2* | 5/2011 | Arramon | A61B 17/3421 606/92 |
| 7,972,339 B2* | 7/2011 | Nassiri | A61B 17/3472 606/92 |
| 2003/0225344 A1* | 12/2003 | Miller | A61B 10/025 600/568 |
| 2005/0159730 A1* | 7/2005 | Kathrani | A61B 17/3421 604/541 |
| 2006/0142779 A1 | 6/2006 | Arramon et al. | |
| 2007/0142842 A1 | 6/2007 | Krueger et al. | |
| 2009/0198243 A1 | 8/2009 | Melsheimer | |

\* cited by examiner

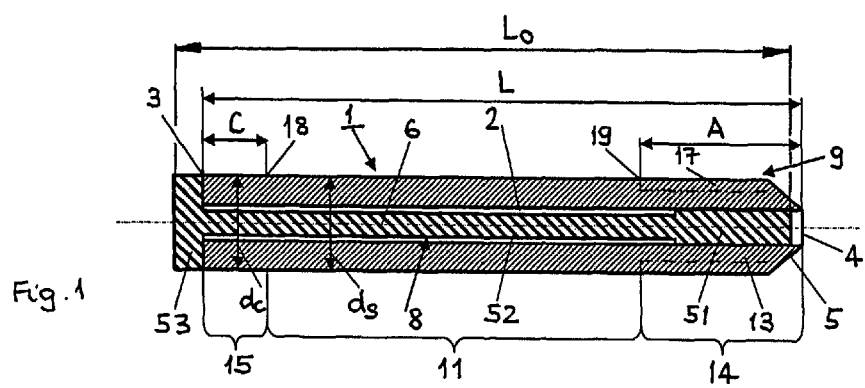
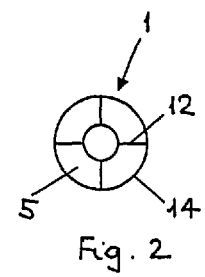
Fig. 1
Fig. 2
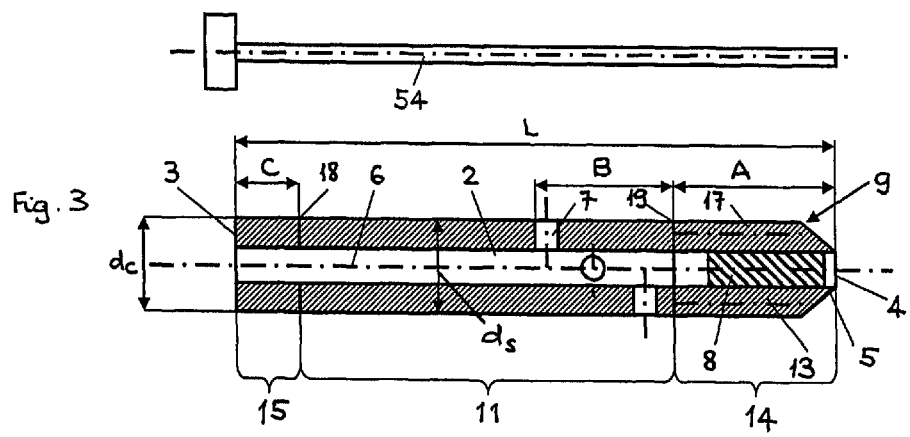
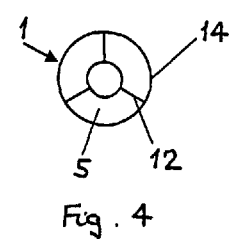
Fig. 3
Fig. 4

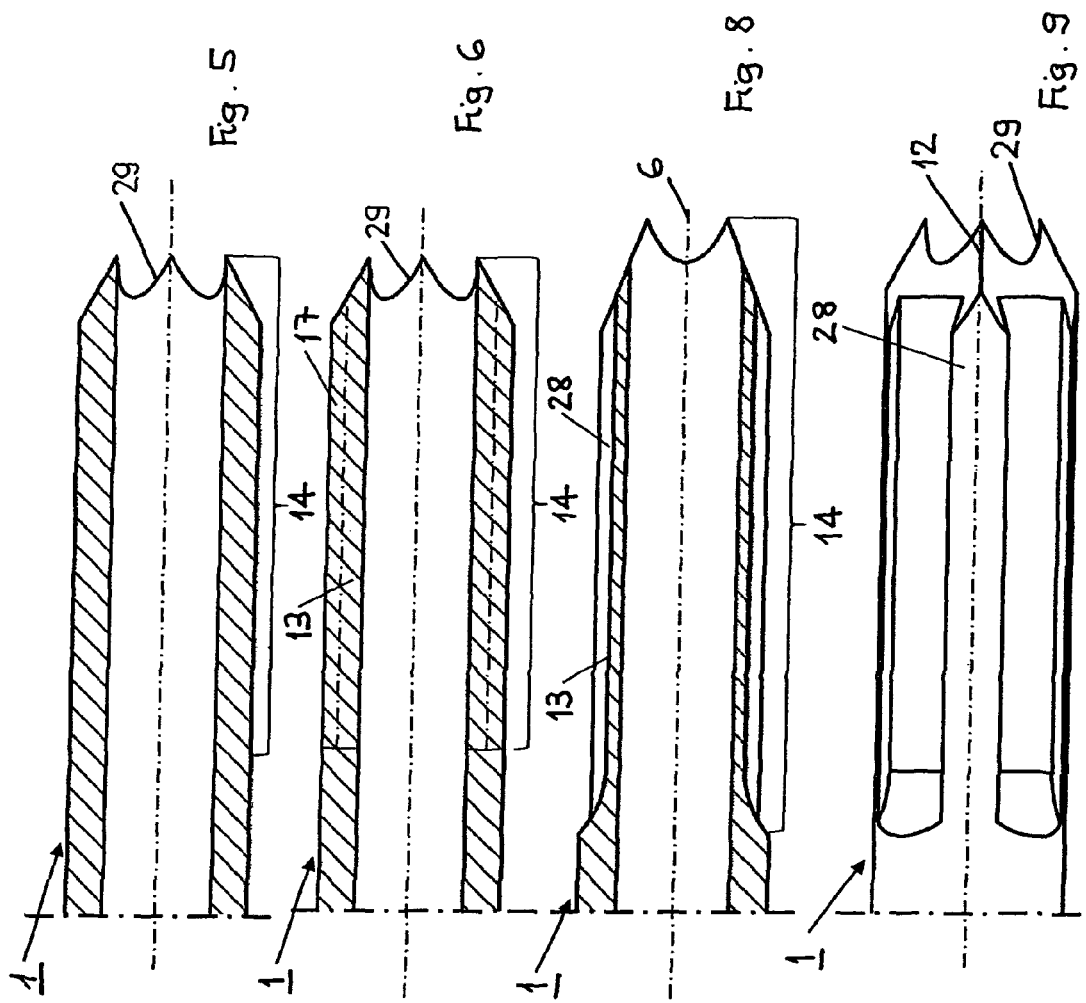
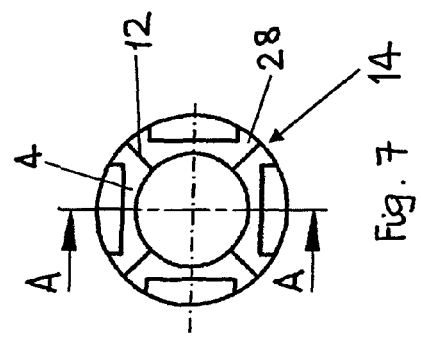

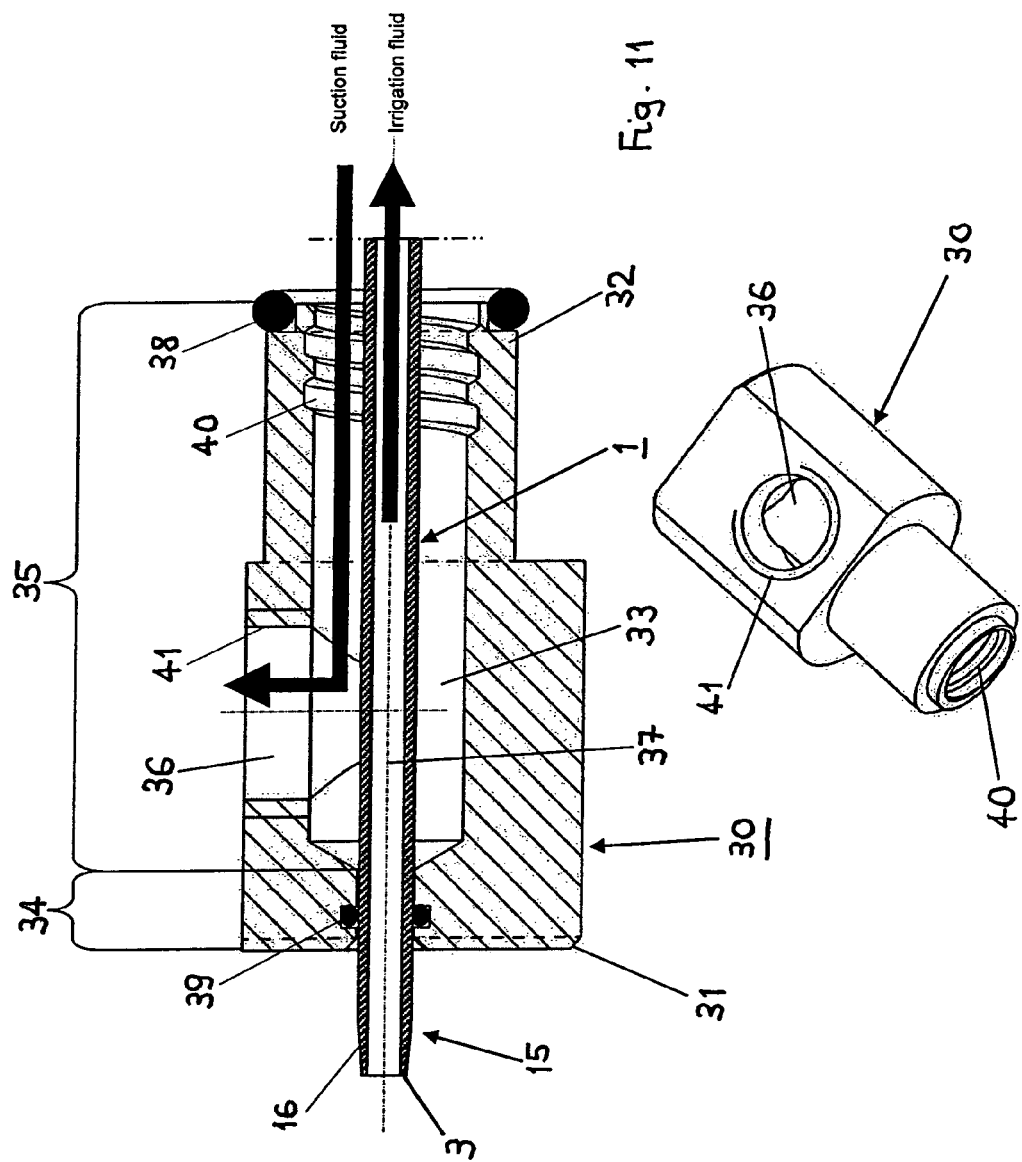

CANNULA AND KIT FOR EVALUATION AND PREPARATION OF BONE TISSUE

The invention relates to a cannula, to a kit for bone cement injection, to a method for improved fracture fixation, to a method for intraoperative surgical decision making and to a method for irrigation of bone tissue and subsequent injection of a bone cement.

Osteosynthesis failure in porotic bone is a growing problem related to current demographic changes. New strategies have been introduced to improve fracture fixation such as augmentation of implants with bone cement, irrigation of bone tissue or acquisition of meaningful parameters with regard to bone quality/viability for surgical decision making prior to implant insertion. A systematic and efficient procedure and toolkit addressing and combining several steps for an improved surgical outcome, with special reference to geriatric fracture care, is still missing.

The augmentation of implants has a high potential to significantly enhance the implant anchorage, but is nowadays only rarely applied due to a missing standard. With individually varying cement application procedures new problems arise relativizing its potential. For instance, cement augmentation is often performed through the cannulation of the implant after its insertion in the bore hole in the bone. A guide wire which usually has been previously inserted for guiding a surgical tool e.g. a drill bit for drilling a bore hole in the bone and the implant has then to be removed. In many cases the guide wire has perforated into the joint leaving a channel between the inner bone and the articulation surfaces. The problem of bone cement advancing into the joint through said channel is not yet solved.

An irrigation procedure to prepare the bone tissue prior to the bone cement insertion (e.g. in the spine) has been proven to be beneficial in terms of reduction of the injection forces, increase of the maximum bone cement volume and removal of fat for preventing fat embolisms. However, no adequate device and procedure exists today for performing these tasks rapidly and minimal invasively.

Before the surgeon takes a decision whether a treatment of the bone tissue with an irrigation procedure and/or with bone cement is to be applied a measurement of the bone quality and/or an assessment of the bone viability, particularly in the area where the implant or prosthesis is fixed in the bone, provides an objective basis for the decision making process.

The complete procedure beginning with drilling a bore hole in the bone, subsequently measuring the bone quality/viability of the bone tissue surrounding the bore hole, eventually performing an irrigation procedure and an application of bone cement before implanting an suitable osteosynthetic implant or prosthesis by using a guide wire fixed to the bone requires the use of several different instruments that have to be subsequently inserted in and removed from the bore hole in the bone.

What is therefore needed is an improved device that permits to significantly reduce the number of different instruments to be inserted in the bore hole in a bone before finally implanting a suitable osteosynthetic implant or prosthesis as well as a standardized method permitting a combined workflow of several steps for improving fracture fixation in porotic bone.

DESCRIPTION OF THE RELATED ART

A device with a cannula for applying a bone cement is known from US-A 2007/0142842 KRUEGER. This known cannula can have an open distal end and comprises a deflectable segment terminating at the distal end of the cannula. Furthermore, the device can include a probe in the form of a guide wire that can be inserted into the cannula to remove blockages that may form within the cannula. Preferably, the probe has a diameter that is smaller than the inner diameter of the cannula to allow material within the cannula to flow around the probe as the probe is inserted into the cannula.

One problem associated with the above described cannula is that the probe does not seal the opening of the lumen at the tip of the cannula so that the lumen of the cannula can become contaminated during insertion of the cannula into bone tissue.

Another cannula for introducing a bone cement mixture is known from US-A 2009/0198243 MELSHEIMER. A lumen is formed through the cannula for advancing the bone cement mixture to the distal portion of the cannula. The distal portion of the cannula is provided with a tip member and with a side aperture proximal to said tip member. The tip member directs the advancement of the bone cement mixture through the side aperture while preventing advancement of the bone cement mixture axially through the distal end of the cannula. However, this known cannula comprises a proximal portion with an enlarged diameter so that the cannula could not be used as a guide wire for a surgical instrument, tool or an implant.

BRIEF SUMMARY OF THE INVENTION

It is an object of the invention to provide a multi-functional cannula which is suitable to be inserted into bone tissue without the need of previously drilling a hole into the bone, which permits to lead and remove a measuring sensor through its lumen and which can be used as a guide wire for surgical instruments, tools and/or an implant.

The invention solves the posed problem with a cannula, with a kit for bone cement injection, with a method for improved fracture fixation, with a method for intraoperative surgical decision making and with a method for irrigation of bone tissue and subsequent injection of a bone cement as disclosed and claimed herein.

The advantages achieved by the cannula according to the invention are essentially to be seen therein that:
- the cannula can be advanced into bone tissue without the need of additional drilling tools in such a way that no bone chips can enter into the lumen of the cannula. The prevention of a contamination of the lumen of the cannula is particularly important when a measuring probe is to be led through the lumen after fixing the cannula in a bone because a contamination of the lumen could lead to faulty measured values. Further, the lumen has to be free of deposits when a sensitive measuring sensor is to be lead through;
- after removal of the obturator the cannula can be used to intraoperatively insert a measuring sensor into the lumen of the cannula to measure one or more measuring quantities that are relevant for the subsequent surgical treatment, as for example the degree of blood circulation as an assistance for making a decision, e.g. to use a prosthesis instead of performing an osteosynthesis. Other measuring sensors can include sensors for measuring oxygenic saturation, blood flow, blood sugar, electrical current and comparable. For example, a glass fibre bundle can be led through the lumen of the cannula after removal of the obturator so that a Laser-Doppler measurement of the intraoperative blood circulation can be performed through opening at the tip of the cannula. This allows to avoid surgical revision operations due to the preceding determination whether the bone fragment has mortified. Other measuring technologies can be infra-red based or comparable;

after removal of the obturator from the cannula a liquid jet irrigation through the cannula can be performed in a bone portion to prepare the bone tissue for a subsequent application of bone cement;

after removal of the obturator from the cannula bone cement can be injected through the lumen so as to augment the surrounding bone tissue before or after an implant has been inserted in the bone tissue;

the cannula can be used as a guide wire for a surgical instrument or tool or for an implant. For example, the cannula allows to replace a guide wire used for placing a bone cement injection device or an implant or tool;

an injection of bone cement can be performed without removing the cannula so that after injection of the bone cement an implant can be inserted over the cannula into the cement volume or an implant can be inserted prior to bone cement application (e.g. a perforated blade for the proximal femur); and the cannula can be used as a drill bit.

Said coupling portion of said cannula can be configured, e.g. as a cone for an attachment of a syringe, jet irrigation device or comparable tool. If said coupling portion has a non-circular cross-section said diameter is to be interpreted as the diameter of the circular cylindrical envelope.

In a special embodiment of the cannula at least in said tip portion said obturator is fixed in said lumen by a press fit. Therewith the advantage can be achieved that the obturator is secured in the cannula. The coupling between the cannula and the obturator cannot loosen so as to prevent the obturator from remaining in the bone or soft tissue when the cannula is removed.

In a further embodiment of the cannula said obturator is made of a non-metallic material, preferably of a bio-resorbable material. This configuration allows the advantage that the obturator can be removed through the opening of the lumen at the tip of the cannula because the material of the obturator can degrade within the surrounding tissue.

In a further embodiment of the cannula said obturator is removable from the proximal end of the cannula. This configuration permits the advantages:

after removal of the obturator from the cannula a liquid jet irrigation through the cannula can be performed in a bone portion to prepare the bone tissue for a subsequent application of bone cement;

after removal of the obturator from the cannula bone cement can be injected through the lumen so as to augment the surrounding bone tissue before or after an implant has been inserted in the bone tissue; and the obturator can have a length $L_o$ which is larger than the length L of the cannula so that the obturator protrudes from the proximal end of the cannula and can be removed from the proximal end of the cannula when the cannula is inserted in a bone.

In a further embodiment of the cannula said obturator is configured as a plug fitting into said lumen in the region of said tip portion of said cannula. The plug can be removed by using a plunger that can be inserted in the lumen of the cannula from the proximal end of the cannula.

In another embodiment of the cannula the obturator does not protrude from the distal end of the cannula. Therewith the advantage can be achieved that the obturator is not mechanically stressed during insertion of the cannula in the bone.

In another embodiment of the cannula said obturator includes no cutting edges. This configuration allows the advantage that the joining between the obturator and the cannula is not mechanically stressed when the cannula is advanced into bone tissue so that the obturator cannot loosen.

In again another embodiment said cannula has no radial perforations.

In yet another embodiment of the cannula said shaft portion comprises one or more radial perforations. This configuration allows the advantage that if the shaft portion comprises one or more radial perforations the removal of the plunger is optional because a washing fluid or bone cement can radially flow through the radial perforations.

In still another embodiment said cannula comprises a plurality of perforations. Said perforations can be arranged angularly symmetrically or angularly asymmetrically when viewed in cross sections orthogonal to said central axis. Said perforations can be arranged in a plurality of planes orthogonal to said central axis, preferably with a parallel orientation with each other. This configuration allows the advantage that a directed irrigation is possible by turning the cannula towards a desired direction. Said perforations can be staggeredly arranged. The outer diameter of said cannula is maximum 8 mm, preferably maximum 3.5 mm.

In a further embodiment said coupling portion has a length C measured from said proximal end of said cannula wherein the ratio C/L between said length C and said overall length L of said cannula amounts to maximum 0.1, preferably maximum 0.05.

In a further embodiment said tip portion comprises a coaxial core and a fixation structure radially protruding from said core suitable to anchor said cannula in a bone. An advantage of this configuration is that the cannula can be firmly anchored with its tip portion in a bone allowing to use the cannula as a guide wire for a surgical instrument or tool or for an implant.

In again a further embodiment of the cannula the tip portion does not radially protrude from the shaft portion so that an implant can be slid over the complete cannula. The tip portion can comprise a fixation structure, e.g. an external thread. The cannula can be pulled out of the central bore of an implant which has been previously implanted by using the cannula as a guide wire.

In another embodiment said tip portion has a length A wherein the ratio A/L between said length A and said overall length L of said cannula is maximum 0.38, preferably maximum 0.025.

In yet another embodiment said fixation structure is formed by one or more blades or one or more lamellas, preferably extending along said central axis. A so configured fixation structure allows a firm anchorage of the cannula in the bone. In a further embodiment said fixation structure can be a helical blade, or a helical lamella or an external thread. The cannula can then be inserted in the bone in a screw-like manner. The diameter of the tip portion including the fixation structure can be equal to or smaller than the diameter of the shaft of the cannula. Further, said fixation structure can comprise two or more blades or lamellas which are offset relative to each other in a direction parallel to said central axis. By means of this configuration of the fixation structure the rigidity of the anchorage of the cannula in the bone can be improved.

Furthermore, the advantage can be achieved that by rotating the cannula including one or more blades or lamellas in the surrounding bone tissue until failure of the bone structure the breakaway torque of the surrounding trabecular bone structure which is used to specify the bone quality can be measured.

In again a further embodiment of the cannula said one or more lamellas comprises an anchoring structure, preferably an external thread.

In a further embodiment said tip portion comprises a plurality of cutting edges. The tip can be configured as a truncated pyramid like spike including three or four cutting edges or can be configured as a drill tip. The aforementioned configuration of the tip of the cannula allows the advantage that the cannula can be advanced into the bone without the need of additional drilling tools. Furthermore, the cannula can be used as a drill.

In another embodiment said length A is maximum 30 mm, preferably maximum 8 mm. The overall length of the cannula is maximum L=400 mm, preferably maximum L=320 mm, while the minimum for the overall length amounts to L=80 mm.

In again another embodiment said at least one radial perforation is located within an axial range with a length B measured from said front end of said shaft wherein the ratio between said length B and said overall length L is maximum 0.5, preferably maximum 0.038. A maximum value for the length is B=40 mm, preferably maximum B=12 mm.

In still a further embodiment said tip portion is self-drilling. The tip portion can comprise a terminal section configured as a drill bit.

In another embodiment said fixation structure is self-tapping.

Said shaft can be prismatical or cylindrical, preferably circular cylindrical. A circular cylindrical shape offers the advantage that the cannula can be used as a guide wire for an instrument, tool or an implant.

In a further embodiment said shaft has a constant diameter $d_s$ and a smooth surface between said coupling portion and said front end of said shaft.

In again a further embodiment of the cannula the coupling portion tapers, preferably conically towards the proximal end of the cannula.

In yet a further embodiment of the cannula said cannula is rigid over its entire overall length L. This configuration allows the advantage that the cannula can be used as a rigid guide wire for guiding surgical instruments, tools and implants.

The advantage achieved by the kit for irrigating bone tissue and subsequent injection of bone cement according to the invention is essentially to be seen therein that the cannula can slide and rotate within the outer tube in order to adjust the direction and position of the jet lavage. The difference between the inner width $D_t$ of the through hole and the outer diameter $d_s$ of the cannula is preferably in a range between 0.2 mm and 4 mm, and typically 0.9 mm. Typically the outer diameter of the cannula is 2.6 mm and the diameter of the through hole is 3.5 mm. The channel between the outer peripheral wall of said cannula and the inner wall of said outer tube can be used for either:
  A) Suction of irrigation fluid;
  B) Insertion of irrigation fluid; or
  C) Injection of a bone cement.

The assembly of said sleeve and said cannula may be used as follows:
  D) insertion of irrigation fluid via the lumen of said cannula;
  E) simultaneous removal of fluid via the sleeve; and
  F) subsequent application of bone cement via the sleeve.

In a further embodiment of said kit said outer tube comprises a lateral aperture. Therewith the advantage can be achieved that the bone cement will mainly advance through the lateral aperture because the axial way will be blocked by compacted bone tissue. An advantage of an axially open outer lumen is the possible motion between the cannula and the outer tube at the tip. If e.g. blood cloths block the channel during suction, a short movement of the assembly could remove this blockage. The outer tube can comprise two or more lateral openings.

In another embodiment said kit further comprises an inner tube axially displaceably arranged in said through hole of said outer tube and comprising a central through bore for rotatively and slideably receiving said cannula. An advantage of this configuration is that the inner tube fitting in between said cannula and said outer tube allows to remove bone tissue, blocking the channel between the wall of the through channel of said outer tube and the peripheral wall of said cannula.

In again another embodiment said kit further comprises an adaptor with a through opening with an enlarged section connectable to said outer tube in fluid communication with said through hole of said outer tube and having an aspiration port in fluid connection with said through opening.

Further advantages that can be achieved by the kit according to the invention are essentially that:
  an irrigation of the bone tissue can be performed through the cannula and the suction of the flushing fluid can be simultaneously realized via the channel in-between the cannula and the bone cement injection sleeve; and
  the instruments used during this surgical procedure as well as the necessary steps for performing said surgical procedure can be reduced to a minimum.

According to a further aspect of the invention an assembly is provided which comprises a cannula according to the invention and a measuring sensor insertable in said lumen of said cannula.

In a special embodiment of the assembly the measuring sensor is a sensor for measuring one or more of the following physical or chemical properties: oxygenic saturation, blood flow, blood sugar or electric current.

The cannula according to the invention can be used for the following purposes individually or cumulatively:
  drilling a hole in a bone;
  guiding an instrument, tool or and/or an implant to be inserted into a bone;
  injecting a washing liquid or injectable biomaterials such as bone cements through said lumen into a bone;
  aspirating a washing liquid or body fluids through said lumen from a bone;
  intraoperative mechanical measurement of the bone quality; and
  intraoperatively measuring the blood circulation in cancellous bone.

In a special embodiment the method for an improved fracture fixation further comprises before step b) the sub-step of:
  a2) measuring of bone viability, particularly bone perfusion after removing the obturator.

For example, a glass fibre bundle can be led through the lumen of the cannula after removal of the obturator so that an intraoperative Laser-Doppler or infra-red based measurement of the blood circulation can be performed through the opening at the tip of the cannula.

For the measuring procedure the cannula is preferably inserted by means of a drilling machine. For measuring the blood circulation the tip of the cannula is preferably inserted to a depth which ideally coincides with the center of a spherical bone portion (e.g. the femoral head or the humeral head). However, this is not a mandatory condition.

In a further embodiment the method for an improved fracture fixation further comprises before step b) the sub-step of:

a3) measuring of bone quality.

The measurement of bone quality can be e.g. a measurement of mechanical bone strength. The breakaway torque which is related to the mechanical bone strength can be measured by rotating the cannula comprising one or more blades or lamellas until failure of the bone structure occurs.

For measuring the breakaway torque the tip portion of the cannula should be positioned at the target position of the implant which is subsequently inserted into the bone. This measurement is therefore dependent on the implant to be used. For measuring the breakaway torque the cannula can be inserted by means of e.g. a drilling machine into the bone as far as 20-30 mm before its targeted position. For the remaining distance the cannula is beat in so that the bone structure is not radially damaged. Subsequently, the cannula is rotated and the maximum torque is recorded.

If the decision of using a bone cement has been previously taken on the basis of computer tomography (CT) or dual-energy X-ray absorptiometry (DXA) a measurement of the bone quality, e.g. the bone density is not necessary to decide whether a bone cement is to be applied or not.

In a further embodiment of the method for an improved fracture fixation step a3) of measuring the bone quality is performed by rotating the cannula according to the invention until failure of the bone structure and measuring the breakaway torque of the surrounding trabecular structure. On the basis of the measured value of the breakaway torque measured under step a3) an intraoperative surgical decision can be taken if an osteosynthetic implant can be used for treatment of the fracture without the need of applying a liquid jet irrigation and/or a bone cement for augmentation or if a liquid jet irrigation and/or bone cement is to be applied. The surgical decision can be based on a database and could be taken by means of a suitably programmed computer if available.

In a further embodiment the method for an improved fracture fixation further comprises before step b) the sub-step of:

a4) irrigating the bone tissue surrounding the cannula by pressing a washing liquid through the lumen of the cannula.

In another embodiment the method for an improved fracture fixation further comprises before step b) the sub-step of:

a5) aspirating the washing fluid and/or body fluids through the lumen of the cannula.

The irrigation performed under step a4) and the aspiration under step a5) can be performed alternatingly.

Alternatively, the irrigation of bone tissue and the aspiration of the washing fluid and/or body fluids can be performed by using an embodiment of the kit according to the invention.

In again another embodiment the method for an improved fracture fixation further comprises the sub-step of:

a6) injecting a bone cement through said lumen in said cannula, wherein the osteosynthetic implant can be positioned after injecting the bone cement so that step a6) is performed before step b); or the osteosynthetic implant can be positioned before injecting the bone cement so that step b) is performed before step a6).

In a special embodiment the method for intraoperative decision making further comprises the steps of:

v) positioning said osteosynthetic implant on said fractured bone by using said cannula as a guide wire;

vi) fixing said bone fracture; and vii) removing said cannula.

In a further embodiment the method for intraoperative decision making further comprises before step v) the sub-step of:

measuring of bone quality.

In a further embodiment of the method for intraoperative decision making the bone quality is measured by rotating the cannula according to the invention until failure of the bone structure and measuring the breakaway torque of the surrounding trabecular structure.

In another embodiment the method for intraoperative decision making further comprises before step v) the sub-step of:

irrigating the bone tissue surrounding the cannula by pressing a washing liquid through the lumen of the cannula.

In again another embodiment the method for intraoperative decision making further comprises before step v) the sub-step of:

aspirating the washing fluid and/or body fluids through the lumen of the cannula.

The irrigation of bone tissue and the aspiration of the washing fluid and/or body fluids can be performed alternatingly.

Alternatively, the irrigation of bone tissue and the aspiration of the washing fluid and/or body fluids can be performed by using an embodiment of the kit according to the invention.

In yet another embodiment the method for intraoperative decision making further comprises before step v) the sub-step of:

injecting a bone cement through said lumen in said cannula, wherein the osteosynthetic implant is positioned after injecting the bone cement;

or wherein the osteosynthetic implant is positioned before injecting the bone cement.

A BRIEF DESCRIPTION OF THE DRAWINGS

Several embodiments of the invention will be described in the following by way of example and with reference to the accompanying drawings in which:

FIG. 1 illustrates a longitudinal section of an embodiment of the cannula according to the invention;

FIG. 2 illustrates a front view of the embodiment of the cannula according to FIG. 1;

FIG. 3 illustrates a longitudinal section of a further embodiment of the cannula according to the invention;

FIG. 4 illustrates a front view of the embodiment of the cannula according to FIG. 3;

FIG. 5 illustrates a longitudinal section of a tip portion of another embodiment of the cannula according to the invention;

FIG. 6 illustrates a longitudinal section of a tip portion of the embodiment of the cannula according to the invention of FIG. 1;

FIG. 7 illustrates a front view of again another embodiment of the cannula according to the invention;

FIG. 8 illustrates a longitudinal section of the tip portion of the embodiment of the cannula according to the invention of FIG. 7 along line A-A in FIG. 7;

FIG. 9 illustrates an elevational view of the tip portion of the embodiment of the cannula according to the invention of FIG. 7;

FIG. 11 illustrates a longitudinal section of an adaptor used with an embodiment of the kit according to the invention;

FIG. 12 illustrates a perspective view of the adaptor of FIG. 6; and

Figure 13:
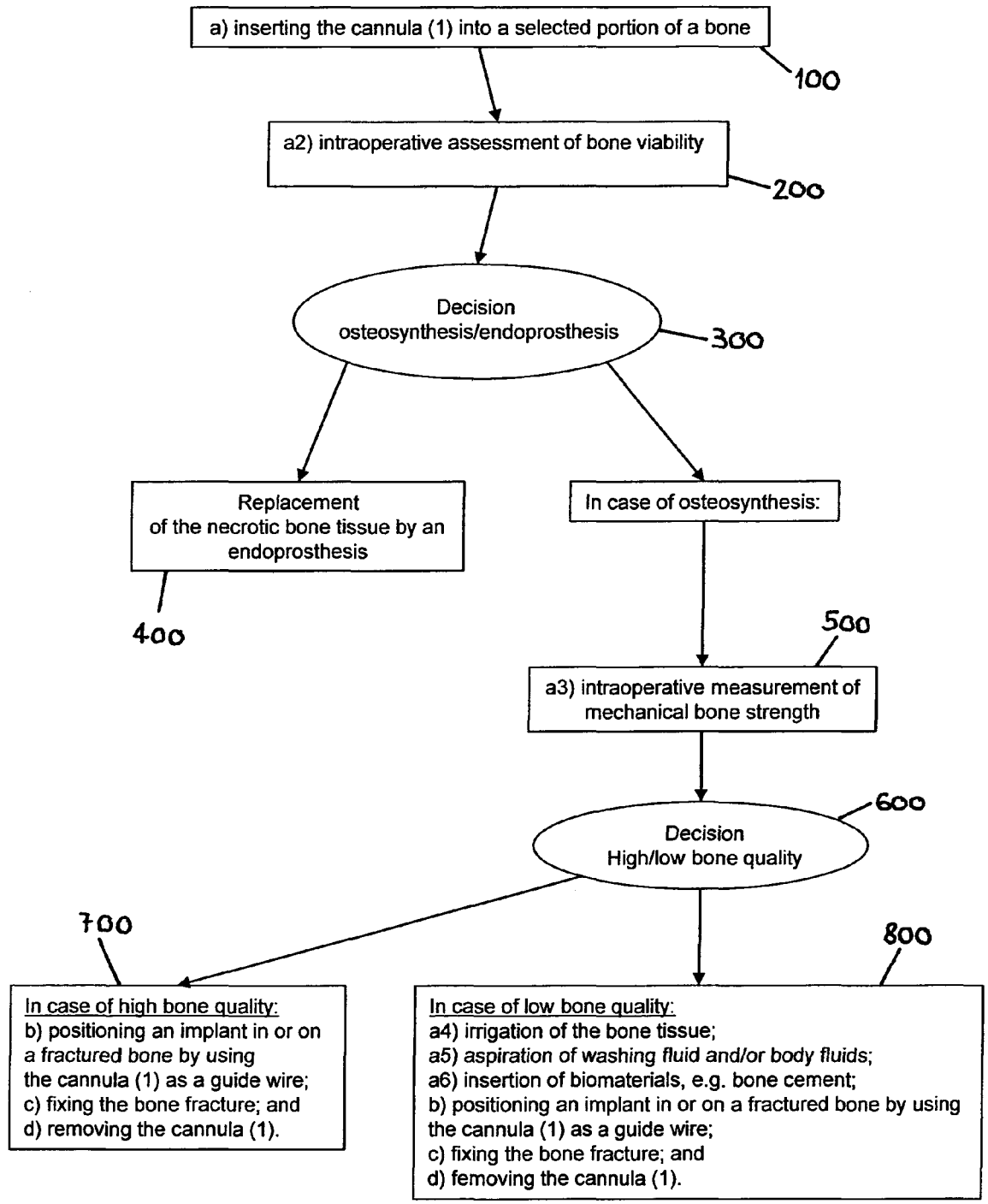

FIG. 13 a block diagram of an embodiment of the method for treatment of a fractured bone according to the invention.

An embodiment of the cannula 1 is illustrated in FIGS. 1 and 2 wherein said cannula 1 comprises integrally formed a cylindrical shaft portion 11, a tip portion 14 and a coupling portion 15. Said cannula 1 has an overall length L, a central axis 6, a proximal end 3, a distal end 4 and a lumen 2 penetrating through said cannula 1 from said proximal end 3 to said distal end 4. Said shaft portion 11 has a smooth peripheral surface and comprises a rear end 18 at the transition to the coupling portion 15 and a front end 19 at the transition to the tip portion 14. Said coupling portion 15 has a length C, is cylindrically shaped and terminally arranged towards said proximal end 3 of said cannula 1 so that a surgical tool or instrument can be connected to said cannula 1. Said shaft 11 has a constant diameter $d_s$ between said coupling portion 15 and said front end 19 and said coupling portion 15 has a diameter $d_c$ which is equal to said diameter $d_s$ of said shaft portion 11. Said tip portion 14 extends from said front end 19 of said shaft 11 coaxially to said central axis 6 and comprises a tip 5 which is configured as a truncated pyramid-like spike with four cutting edges 12 (FIG. 2) which are arranged at equal angles with respect to each other measured about said central axis 6. Furthermore, said tip portion 14 is hollow so that said cannula 1 is axially open at said distal end 4 of said cannula 1. Said tip portion 14 extends over an axial length A and comprises an external thread 17. Said external thread forms a fixation means with a coaxial core 13 and a fixation structure 9 radially protruding from said core 13 so that said cannula 1 can be firmly anchored in a bone. In the present embodiment the outer diameter of said tip portion 14 is equal to the diameter $d_s$ of said shaft 11.

The cannula 1 further comprises a removable obturator 8 that is insertable in said lumen 2 and seals said lumen 2 at the distal end 4 of the cannula 1 when inserted into said lumen 2. The obturator 8 includes a sealing plug 51 axially terminally arranged towards a first end, a coaxial shaft 52 and a head 53 axially terminally arranged towards a second end. The head 53 has a diameter that is larger than the diameter of the lumen 2 of the cannula 1. The sealing plug 51, the shaft 52 and the head 53 of the obturator 8 can be integrally formed. The sealing plug 51 is fixed in the lumen 2 in the region of the tip portion 14 of the cannula 1 by a press fit. The obturator 8 has a length $L_o$ which is larger than the length L of the cannula 1.

When the obturator 8 is inserted into the lumen 2 of the cannula 1 the head 53 of the obturator 8 abuts on the proximal end 3 of the cannula 1 so that the sealing plug 51 is located completely inside the cannula 1 and does not protrude from the distal end 4 of the cannula 1. Thus, the obturator 8 is not mechanically stressed during insertion of the cannula 1 in a bone. The obturator 8 can be removed from the proximal end 3 of the cannula 1 when the cannula 1 is inserted into a bone.

FIGS. 3 and 4 illustrate another embodiment of the cannula 1 which differs from the embodiment of FIGS. 1 and 2 only therein that said shaft portion 11 includes a plurality of radial perforations 7, said tip portion 14 comprises three cutting edges 12 instead of four cutting edges 12 and the obturator 8 is configured as a plug fitting into said lumen 2 in the region of said tip portion 14 of said cannula 1. The three cutting edges 12 are arranged at equal angles with respect to each other measured about said central axis 6 (FIG. 4). Similarly to the embodiment of FIGS. 1 and 2 said tip portion 14 extends over an axial length A and comprises an external thread 17.

Said plurality of radial perforations 7 are located within an axial range with a length B measured from said front end 19 of said shaft 11 towards the proximal end 3 of the cannula 1. Further, said radial perforations 7 are located at different distances measured from said front end 19 of said shaft 11 and are arranged with their hole axes at equal angles relative to each other measured in a plane of projection orthogonal to said central axis 6 of said cannula 1. The plug like obturator 8 is fixed in the lumen 2 in the region of the tip portion 14 of the cannula 1 by a press fit. The obturator 8 can be made of a non-metallic material, preferably of a bioresorbable material so that it can be pushed out of the lumen 2 at the distal end 4 of the cannula 1 when the cannula 1 is inserted in a bone by means of a plunger 54. The plunger 54 can be lead through the lumen 2 of the cannula 1 from the proximal end 3 and removed when the obturator 8 has been pushed out of the lumen 2.

FIGS. 5 to 9 illustrate a variety of tip portions 14 of different embodiments of the cannula 1. Each of the embodiments of the cannula 1 illustrated in FIGS. 1 to 4 can comprise—as an alternative to the tip portions 14 illustrated in FIGS. 1 to 4—an embodiment of the tip portion 14 illustrated in FIGS. 5 to 9.

The embodiment of the tip portion 14 illustrated in FIG. 5 does not comprise a particular fixation structure 9. The tip portion 14 is an extension of the shaft portion 11 and has the same diameter as the shaft portion 11. Similarly to the embodiments of the tip portions 14 according to FIGS. 1 to 4 the tip portion 14 is configured as a truncated pyramid-like spike with four cutting edges 12 at the edges of the pyramid-like spike. Additionally, the tip portion 14 has frontally arranged a plurality of saw-teeth 29 to improve the cutting quality of the tip portion 14.

The embodiment of the tip portion 14 of FIG. 6 differs from the embodiment of FIGS. 1 to 4 only therein that it additionally comprises a plurality of frontally arranged saw-teeth 29.

The embodiment of the tip portion 14 of FIGS. 7 to 9 comprises a core 13 extending coaxially to the central axis 6 of the cannula 1 and four lamellas 28 radially protruding from the core 13 and extending along the longitudinal axis 6 of the cannula 1. Similarly to the embodiments of the tip portion 14 illustrated in FIGS. 1 to 4 the tip portion 14 is configured as a truncated pyramid-like spike with four cutting edges 12 spaced apart from each other by equal angles and extending at the edges of the pyramid-like spike. The cutting edges 12 extend from the outer surface of the lamellas 28 to the tip 5 of the cannula 1. Additionally the tip portion 14 comprises a plurality of frontally arranged saw-teeth 29.

Figure 10:
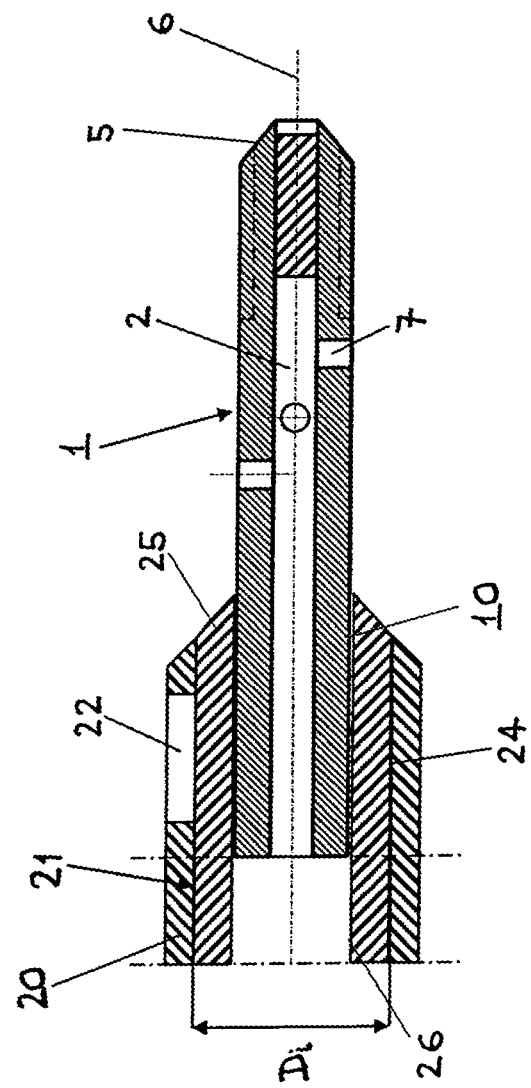
FIG. 10 illustrates a longitudinal section of an embodiment of the kit according to the invention.

FIG. 10 illustrates an embodiment of the kit for irrigating bone tissue and subsequent injection of bone cement including the embodiment of the cannula 1 of FIGS. 3 and 4 and an outer tube 20 with a through hole 21 of diameter $D_i$ for injection of bone cement. Said cannula 1 is rotatably and axially displaceably arranged in said through hole 21. Further, said outer tube 20 comprises a lateral aperture 22 wherethrough a bone cement injected through said through hole 21 will mainly advance. The channel between the outer peripheral wall 10 of said cannula 1 and the inner wall 24 of said outer tube 20 can be used for either suction of irrigation fluid, insertion of irrigation fluid or injection of bone cement. The kit further comprises an inner tube 25 which is axially displaceably arranged in said through hole 21 of said outer tube 20. Further, said inner tube 25 comprises a central through bore 26 for rotatively and slideably receiving said cannula 1. Said inner tube 25 fits in between said cannula 1 and said outer tube 20.

FIGS. 11 and 12 illustrate an adaptor 30 to be used in another embodiment of the kit according to the invention. Said adaptor 30 essentially comprises a first end 31, a second end 32 and a through opening 33 extending between said first and second end 31, 32. Said through opening 33 has a longitudinal axis 37, a coaxial first section 34 for guiding said cannula 1 and a coaxial second section 35 with a larger diameter which is suitable for fluid connection with the through hole 21 of said outer tube 20 (FIG. 10). An aspiration port 36 is arranged transversely to said longitudinal axis 37 and in fluid connection with said second section 35 of said through opening 33. Said second section 35 of said through opening 33 comprises a female Luer-Lock connector 40 at said second end 32 of said adaptor 30 which is connectable to a male Luer-Lock connector at the rear end of said outer tube 20 (not shown). A first sealing 38 is arranged between said second end 32 of said connector 30 and said outer tube 20 to provide a fluid tight transition between said adaptor 30 and said outer tube 20. A second sealing 39 is arranged in said first section 34 of said through hole 33 encircling said cannula 1 to provide a fluid tight closing of said through opening 33 towards said first end 31 of said adaptor 30. Further, said aspiration port 36 comprises a fastening means, e.g. in the form of an internal thread 41 to reversibly fix an aspiration tube thereto. In the present embodiment said coupling portion 15 of said cannula 1 is configured as a cone 16 tapering towards said proximal end 3 of said cannula 1. Said conical coupling portion is used for an attachment of a jet irrigation device.

The above configuration of said adaptor 30 allows to connect an irrigation source (not shown) to the coupling portion 15 of said cannula 1 in such a manner that the irrigation fluid can be pressed through the lumen 2 of said cannula 1. A fluid suction source can be connected to said aspiration port 36 allowing to simultaneously remove the suction fluid from the irrigated bone through said through hole 21 of said outer tube 20 and through said aspiration port 36.

Method for Improved Fracture Fixation of a Bone:

FIG. 13 illustrates a first embodiment of the method for improved fracture fixation of a bone by using the cannula 1 to FIGS. 1-11. The first embodiment of the method comprises the steps of:

a) inserting the cannula 1 into a selected portion of a bone forming a hole in said bone as indicated by block 100;

a2) intraoperative assessment of bone viability, e.g. bone perfusion as indicated by block 200. The assessment of bone viability can be performed by effecting the sub-steps of:

removing the obturator 8 from the cannula 1;

inserting a measuring sensor into the lumen 2 of said cannula 1;

measuring one or more physical or chemical properties related to the bone viability by means of said measuring sensor. The measuring sensor can include a sensor for e.g. measuring oxygenic saturation, blood flow, blood sugar, electrical current and comparable. For example, a glass fibre bundle can be led through the lumen 2 of the cannula 1 so that a Laser-Doppler measurement of the intraoperative blood circulation can be performed through the opening at the tip 5 of the cannula 1. Other measuring technologies can be infra-red based or comparable; and deciding on the basis of the measured one or more physical or chemical property whether an osteosynthesis shall be performed or whether the necrotic bone tissue shall be replaced by an endoprosthesis or alternative treatment options shall be considered as indicated by block 300. The surgical decision can be based on a database and can be taken by the surgeon or e.g. by means of a suitably programmed computer if available; and If the necrotic bone tissue shall be replaced by an endoprosthesis 400 or alternative treatment options shall be considered the cannula 1 can be removed; or if an osteosynthesis shall be performed to following steps can be effected:

a3) measuring of bone quality, e.g. by an intraoperative measurement of the mechanical bone strength as indicated by block 500. The bone quality can be measured, e.g. by rotating the cannula 1 including one or more blades or one or more lamellas 28 until failure of the bone structure and measuring the breakaway torque of the surrounding trabecular structure;

deciding whether an osteosynthetic implant can be used for treatment of the fracture without the need of applying a liquid jet irrigation and/or a bone cement for augmentation or whether a liquid jet irrigation and/or bone cement is to be applied as indicated by block 600. The surgical decision can be based on a database and can be taken by the surgeon or e.g. by means of a suitably programmed computer if available;

if a high bone quality is measured the following steps can be performed as indicated by block 700:

b) positioning an osteosynthetic implant in or on said fractured bone by using said cannula 1 as a guide wire;

c) fixing the bone fracture; and d) removing said cannula 1; or if a low bone quality is measured the following steps can be performed as indicated by block 800:

a4) irrigating the bone tissue surrounding the cannula 1 by pressing a washing liquid through the lumen 2 of the cannula 1;

a5) aspirating the washing fluid and/or body fluids through the lumen 2 of the cannula 1, wherein the irrigation performed under step a4) and the aspiration under step a5) can be performed alternatingly;

a6) injecting a bone cement through said lumen 2 in said cannula 1;

b) positioning an osteosynthetic implant in or on said fractured bone by using said cannula 1 as a guide wire;

c) fixing the bone fracture; and d) removing said cannula 1.

The sequence of steps a6) and b) depends on the implant and the surgeons requirements. The bone cement can be injected before the implant is positioned. Alternatively, the implant can be firstly positioned over said cannula 1 into said bone by using said cannula 1 as a guide wire and secondly a bone cement can be injected through the cannula and through lateral perforations in said implant. In this case the above step b) of positioning an implant over said cannula 1 is performed before step a6) of injecting a bone cement through said lumen 2 in said cannula 1. The latter order of steps b) and a6) can be selected due to safety issues. Many surgeons believe that it is absolutely necessary to firstly insert the implant and then the bone cement to exclude the case of missing the implant insertion during the hardening time of the cement. This however requires then special implants like a perforated blade or screw.

Furthermore, step a4) including the irrigation of the bone tissue and step a5) including the aspiration of the washing fluid and/or body fluids are optional and can be omitted if this treatment of the bone tissue is not necessary.

As will be understood by those skilled in the art the method for improved fracture fixation of a bone does not mandatorily include every step of the above described first embodiment of the method. Therefore, by way of example but not limited to the following variety of embodiments of related methods using only a part of the steps of the first embodiment of the method for improved fracture fixation can be performed.

The decision whether an osteosynthesis is to be performed and whether a bone cement is to be used can be previously taken, e.g. on the basis of computer tomography (CT) or dual-energy X-ray absorptiometry (DXA). In this case an intraoperative measurement of the bone quality, e.g. the bone density or mechanical bone strength is not necessary to decide whether a bone cement is to be applied or not.

Therefore, a second embodiment of the method for improved fracture treatment in case of a high bone quality can comprise the steps indicated by blocks 100 and 700, namely:
a) inserting the cannula 1 into a selected portion of a bone forming a hole in said bone;
b) positioning an osteosynthetic implant in or on said fractured bone by using said cannula 1 as a guide wire;
c) fixing the bone fracture; and
d) removing said cannula 1.

Alternatively, in case of a low bone quality a third embodiment of the method for improved fracture treatment can comprise the steps indicated by blocks 100 and 800, namely:
a) inserting the cannula 1 into a selected portion of a bone forming a hole in said bone;
a4) irrigating the bone tissue surrounding the cannula (1) by pressing a washing liquid through the lumen (2) of the cannula (1);
a5) aspirating the washing fluid and/or body fluids through the lumen (2) of the cannula (1), wherein the irrigation performed under step a4) and the aspiration under step a5) can be performed alternatingly;
a6) injecting a bone cement through said lumen 2 in said cannula 1;
b) positioning an osteosynthetic implant in or on said fractured bone by using said cannula 1 as a guide wire;
c) fixing the bone fracture; and
d) removing said cannula 1.

Alternatively, the implant can be positioned before the bone cement is injected. In this case steps a6) and b) are performed in the following sequence:
b) positioning an osteosynthetic implant in or on said fractured bone by using said cannula 1 as a guide wire; and
a6) injecting a bone cement through said lumen 2 in said cannula 1.

Similarly to the first embodiment of the method step a4) including the irrigation of the bone tissue and step a5) including the aspiration of the washing fluid and/or body fluids are optional and can be omitted if this treatment of the bone tissue is not necessary.

Method for Intraoperative Surgical Decision Making:

The method for intraoperative surgical decision making by using a cannula 1 according to the invention can comprise the following steps:
a) inserting said cannula 1 into a selected portion of a bone forming a hole in said bone as indicated by block 100;
a2) intraoperative assessment of bone viability as indicated by block 200. The assessment of bone viability can be performed by effecting the sub-steps of:
  removing the obturator 8 from the cannula 1;
  inserting a measuring sensor into the lumen 2 of said cannula 1;
  measuring one or more physical or chemical properties related to the bone viability by means of said measuring sensor. The measuring sensor can include a sensor for e.g. measuring oxygenic saturation, blood flow, blood sugar, electrical current and comparable. For example, a glass fibre bundle can be led through the lumen 2 of the cannula 1 so that a Laser-Doppler measurement of the intraoperative blood circulation can be performed through the opening at the tip 5 of the cannula 1. Other measuring technologies can be infra-red based or comparable;
deciding on the basis of the measured one or more physical or chemical property whether an osteosynthesis shall be performed or whether the necrotic bone tissue shall be replaced by an endoprosthesis or alternative treatment options shall be considered as indicated by block 300.

If an osteosynthesis is to be performed the following steps can be performed:
a3) measuring of bone quality, e.g. by an intraoperative measurement of the mechanical bone strength as indicated by block 500. The bone quality can be measured, e.g. by rotating the cannula 1 including one or more blades or one or more lamellas 28 until failure of the bone structure and measuring the breakaway torque of the surrounding trabecular structure;
deciding whether an osteosynthetic implant can be used for treatment of the fracture without the need of applying a liquid jet irrigation and/or a bone cement for augmentation or whether a liquid jet irrigation and/or bone cement is to be applied as indicated by block 600. The surgical decision can be based on a database and could be taken by means of a suitably programmed computer if available;
if a high bone quality is measured the following steps can be performed as indicated by block 700:
b) positioning an osteosynthetic implant in or on said fractured bone by using said cannula 1 as a guide wire;
c) fixing the bone fracture; and
d) removing said cannula 1; or
if a low bone quality is measured the following steps can be performed as indicated by block 800:
a4) irrigating the bone tissue surrounding the cannula 1 by pressing a washing liquid through the lumen 2 of the cannula 1;
a5) aspirating the washing fluid and/or body fluids through the lumen 2 of the cannula 1, wherein the irrigation performed under step a4) and the aspiration under step a5) can be performed alternatingly;
a6) injecting a bone cement through said lumen 2 in said cannula 1;
b) positioning an osteosynthetic implant in or on said fractured bone by using said cannula 1 as a guide wire;
c) fixing the bone fracture; and
d) removing said cannula 1.

As mentioned above the sequence of steps a6) and b) depends on the implant and the surgeons requirements so that alternatively an implant can be firstly positioned over said cannula 1 into said bone by using said cannula 1 as a guide wire and secondly a bone cement can be injected through the cannula 1 and the lateral perforations in said implant. Step b) is then performed before step a6).

Furthermore, step a4) including the irrigation of the bone tissue and step a5) including the aspiration of the washing fluid and/or body fluids are optional and can be omitted if this procedure of the bone tissue is not necessary.

Method for Irrigation of Bone Tissue and Subsequent Injection of a Bone Cement, Particularly in Case of Vertebroplasty:

A method for irrigation of bone tissue and subsequent injection of a bone cement, particularly in case of vertebroplasty by using a kit according to the invention can comprise the following steps:

- inserting said cannula 1 into a selected portion of a bone forming a hole in said bone;
- inserting said inner tube 25 into said through hole 21 of said outer tube 20;
- advancing said outer tube 20 together with said inner tube 25 over said cannula 1 into a cavity in a bone using said cannula 1 as a guide wire;
- removing said inner tube 25;
- irrigating the bone tissue surrounding said cannula 1 by pressing a washing liquid through said lumen 2 of said cannula 1;
- sucking off the washing liquid through said through hole 21 in said outer tube 20 simultaneously to irrigating said bone tissue by means of said cannula 1;
- removing said cannula 1;
- injecting a bone cement through said through hole 21 in said outer tube 20; and
- removing said outer tube 20.

While various descriptions of the present invention are described above, it should be understood that the various features can be used singly or in any combination thereof. The scope of the present invention is accordingly defined as set forth in the appended claims.

The invention claimed is:

1. A cannula with a central axis, a proximal end, a distal end, a lumen penetrating through said cannula from said proximal end to said distal end and an overall length L; said cannula comprising:
   a shaft portion comprising a rear end and a front end;
   a tip portion coaxially extending from said front end of said shaft portion to said distal end of said cannula and including a cutting edge;
   a coupling portion terminally arranged towards said proximal end of said cannula and extending to said rear end of said shaft portion suitable for being connected to a surgical tool or instrument; and
   a removable obturator insertable in said lumen, said obturator being configured as a plug fitting into said lumen in a region of said tip portion of said cannula and being configured to be pushed out of the lumen at the distal end;
   wherein
   said shaft portion has a diameter $d_s$ and said coupling portion has a maximum diameter $d_c$ which is equal to or smaller than said diameter $d_s$ of said shaft portion;
   said obturator seals said lumen at the distal end of the cannula; and
   at least in said tip portion said obturator is fixed in said lumen by a press fit.

2. The cannula according to claim 1, wherein said obturator is made of a non-metallic material.

3. The cannula according to claim 2, wherein said obturator is made of a bioresorbable material.

4. The cannula according to claim 1, wherein the obturator does not protrude from the distal end of the cannula.

5. The cannula according to claim 1, wherein said obturator includes no cutting edges.

6. The cannula according to claim 1, wherein said cannula has no radial perforations.

7. The cannula according to claim 1, wherein said shaft portion comprises one or more radial perforations.

8. The cannula according to claim 7, wherein said one or more radial perforations is located within an axial range with a length B measured from said front end of said shaft portion and wherein the ratio between said length B and said overall length L is a maximum of 0.5.

9. The cannula according to claim 1, wherein said coupling portion has a length C measured from said proximal end of said cannula and wherein the ratio C/L between said length C and said overall length L of said cannula amounts to a maximum of 0.1.

10. The cannula according to claim 1, wherein said tip portion comprises a coaxial core and a fixation structure radially protruding from said core suitable to anchor said cannula in a bone.

11. The cannula according to claim 10, wherein said fixation structure has a length A and wherein the ratio A/L between said length A and said overall length L of said cannula is a maximum of 0.38.

12. The cannula according to claim 11, wherein said length A is maximum of 30 mm.

13. The cannula according to claim 10, wherein said fixation structure is formed by one or more blades or one or more lamellas.

14. The cannula according to claim 13, wherein said one or more lamellas comprises an anchoring structure.

15. The cannula according to claim 10, wherein said fixation structure is self-tapping.

16. The cannula according to claim 1, wherein the tip portion does not radially protrude from the shaft portion.

17. The cannula according to claim 1, wherein said tip portion comprises a plurality of cutting edges.

18. The cannula according to claim 1, wherein said tip portion is self-drilling.

19. The cannula according to claim 1, wherein said shaft portion has a constant diameter $d_s$ and a smooth surface between said coupling portion and said front end of said shaft portion.

20. The cannula according to claim 1, wherein the coupling portion tapers towards the proximal end of the cannula.

21. The cannula according to claim 1, wherein said cannula is rigid over its entire overall length L.

22. A kit for irrigating bone tissue and subsequent injection of bone cement using a cannula according to claim 1 and comprising an outer tube with a through hole for injection of bone cement, wherein said cannula is rotatably and axially displaceably arranged in said through hole.

23. The kit according to claim 22, wherein said outer tube comprises a lateral aperture.

24. The kit according to claim 22, wherein said kit further comprises an inner tube axially displaceably arranged in said through hole of said outer tube and comprising a central through bore for rotatively and slideably receiving said cannula.

25. The kit according to claim 22, wherein said kit further comprises an adaptor with a through opening with an enlarged section connectable to said outer tube in fluid communication with said through hole of said outer tube and having an aspiration port in fluid connection with said through opening.

26. A Method for irrigation of bone tissue and subsequent injection of a bone cement using a kit according to claim 22 comprising the following steps:
    inserting said cannula into a selected portion of a bone forming a hole in said bone;
    inserting an inner tube into said through hole of said outer tube;
    advancing said outer tube together with said inner tube over said cannula into a cavity in a bone using said cannula as a guide wire;
    removing said inner tube;
    irrigating the bone tissue surrounding said cannula by pressing a washing liquid through said lumen of said cannula;
    sucking off the washing liquid through said through hole in said outer tube simultaneously to irrigating said bone tissue by means of said cannula;
    removing said cannula;
    injecting a bone cement through said through hole in said outer tube; and
    removing said outer tube.

27. An assembly comprising a cannula according to claim 1 and a measuring sensor insertable in said lumen of said cannula.

28. The assembly according to claim 27, wherein said measuring sensor is a sensor for measuring one or more of the following physical or chemical properties: oxygenic saturation, blood flow, blood sugar or electric current.

29. A method for improved fracture fixation comprising the steps of:
    inserting a cannula according to claim 1 into a selected portion of a bone forming a hole in said bone;
    positioning an osteosynthetic implant in or on said fractured bone by using said cannula as a guide wire;
    fixing the bone fracture; and
    removing said cannula.

30. The method according to claim 29 further comprising, before the positioning step, measuring bone viability after removing the obturator.

31. The method according to claim 29 further comprising, before the positioning step, measuring bone quality.

32. The method according to claim 31, wherein the tip portion of the cannula comprises a coaxial core and a fixation structure radially protruding from said core suitable to anchor said cannula in a bone, wherein said fixation structure is formed by one or more blades or one or more lamellas, and wherein the step of measuring bone quality is performed by rotating the cannula until failure of the bone structure and measuring the breakaway torque of the surrounding trabecular structure.

33. The method according to claim 29 further comprising, before the positioning step, irrigating the bone tissue surrounding the cannula by pressing a washing liquid through the lumen of the cannula.

34. The method according to claim 33 further comprising, before the positioning step, aspirating the washing fluid or body fluids through the lumen of the cannula.

35. The method according to claim 29 further comprising injecting a bone cement through said lumen in said cannula, wherein
    the osteosynthetic implant can be positioned after injecting the bone cement so that the injecting step is performed before the positioning step; or
    the osteosynthetic implant can be positioned before injecting the bone cement so that the positioning step is performed before the injecting step.

36. A method for intraoperative surgical decision making comprising the following steps:
    inserting a cannula according to claim 1 into a selected portion of a bone forming a hole in said bone;
    inserting a measuring sensor into the lumen of said cannula;
    measuring one or more physical or chemical properties related to bone viability using said measuring sensor;
    deciding on the basis of the measured one or more physical or chemical properties whether an osteosynthesis shall be performed or whether necrotic bone tissue shall be replaced by an endoprosthesis or alternative treatment options shall be considered.

37. The method according to claim 36 further comprising the steps of:
    positioning an osteosynthetic implant on a fractured bone by using said cannula as a guide wire;
    fixing said bone fracture; and
    removing said cannula.

38. The method according to claim 37 further comprising before the positioning step, injecting a bone cement through said lumen in said cannula, wherein
    the osteosynthetic implant is positioned after injecting the bone cement;
    or wherein
    the osteosynthetic implant is positioned before injecting the bone cement.

39. The method according to claim 36 further comprising, before the positioning step, measuring bone quality.

40. The method according to claim 39, wherein the tip portion of the cannula comprises a coaxial core and a fixation structure radially protruding from said core suitable to anchor said cannula in a bone, wherein said fixation structure is formed by one or more blades or one or more lamellas, and wherein the step of measuring bone quality is performed by rotating the cannula until failure of the bone structure and measuring the breakaway torque of the surrounding trabecular structure.

41. The method according to claim 36 further comprising, before the positioning step, irrigating the bone tissue surrounding the cannula by pressing a washing liquid through the lumen of the cannula.

42. The method according to claim 41 further comprising, before the positioning step, aspirating the washing fluid or body fluids through the lumen of the cannula.

* * * * *